(12) United States Patent
Denyer et al.

(10) Patent No.: US 7,748,382 B2
(45) Date of Patent: Jul. 6, 2010

(54) INHALATION METHOD AND APPARATUS

(75) Inventors: Jonathan S. H. Denyer, Chichester (GB); Ivan R. Prince, Chichester (GB)

(73) Assignee: Respironics (UK) Ltd, West Sussex (GB)

( * ) Notice: Subject to any disclaimer, the term of this patent is extended or adjusted under 35 U.S.C. 154(b) by 1121 days.

(21) Appl. No.: 10/535,597

(22) PCT Filed: Nov. 20, 2003

(86) PCT No.: PCT/GB03/05048

§ 371 (c)(1),
(2), (4) Date: Apr. 11, 2006

(87) PCT Pub. No.: WO2004/045689

PCT Pub. Date: Jun. 3, 2004

(65) Prior Publication Data

US 2006/0243277 A1 Nov. 2, 2006

(30) Foreign Application Priority Data

Nov. 20, 2002 (GB) ................................. 0227105.4

(51) Int. Cl.
*F16K 31/02* (2006.01)
(52) U.S. Cl. ................ 128/204.21; 128/204.18; 128/200.24; 128/204.23; 128/204.26
(58) Field of Classification Search ............ 128/204.21, 128/200.24, 202.22, 203.13, 203.14, 204.18, 128/204.23, 204.26; 600/529, 538; 604/23, 604/26, 890.1, 65–67; 434/238, 236, 262
See application file for complete search history.

(56) References Cited

U.S. PATENT DOCUMENTS

| 4,677,975 | A | | 7/1987 | Edgar et al. |
| 4,984,158 | A | * | 1/1991 | Hillsman ............... 128/200.14 |
| 5,020,527 | A | * | 6/1991 | Dessertine ............ 128/200.23 |
| 5,333,106 | A | * | 7/1994 | Lanpher et al. ............. 600/538 |
| 5,363,842 | A | * | 11/1994 | Mishelevich et al. ... 128/200.14 |
| 5,404,871 | A | | 4/1995 | Goodman et al. |
| 5,713,349 | A | | 2/1998 | Keaney |
| 5,906,202 | A | | 5/1999 | Schuster et al. |
| 5,928,156 | A | * | 7/1999 | Krumbiegel et al. ......... 600/529 |
| 6,119,953 | A | | 9/2000 | Ganan-Calvo et al. |
| 6,240,920 | B1 | * | 6/2001 | Strom ................... 128/204.23 |
| 7,073,499 | B1 | * | 7/2006 | Reinhold et al. ........ 128/200.18 |
| 2002/0104532 | A1 | | 8/2002 | Christrup et al. |
| 2003/0205229 | A1 | * | 11/2003 | Crockford et al. ...... 128/204.23 |

FOREIGN PATENT DOCUMENTS

| EP | 0 824 023 A1 | 2/1998 |
| EP | 0 627 266 B1 | 8/1999 |
| EP | 1 142 600 A1 | 10/2001 |

(Continued)

*Primary Examiner*—Steven O Douglas
*Assistant Examiner*—Colin Stuart
(74) *Attorney, Agent, or Firm*—Timothy A. Nathan

(57) ABSTRACT

Signals may be generated in a drug delivering apparatus through which a person inhales to generate a inhaled airstream to signal to the person to cease inhalation after a pre-set period of time has elapsed from detection of the commencement breathing by that person. The pre-set period of time for subsequent inhalations is adjusted depending on the time the person takes to stop inhaling after being signalled.

27 Claims, 8 Drawing Sheets

FOREIGN PATENT DOCUMENTS

Figure 1:
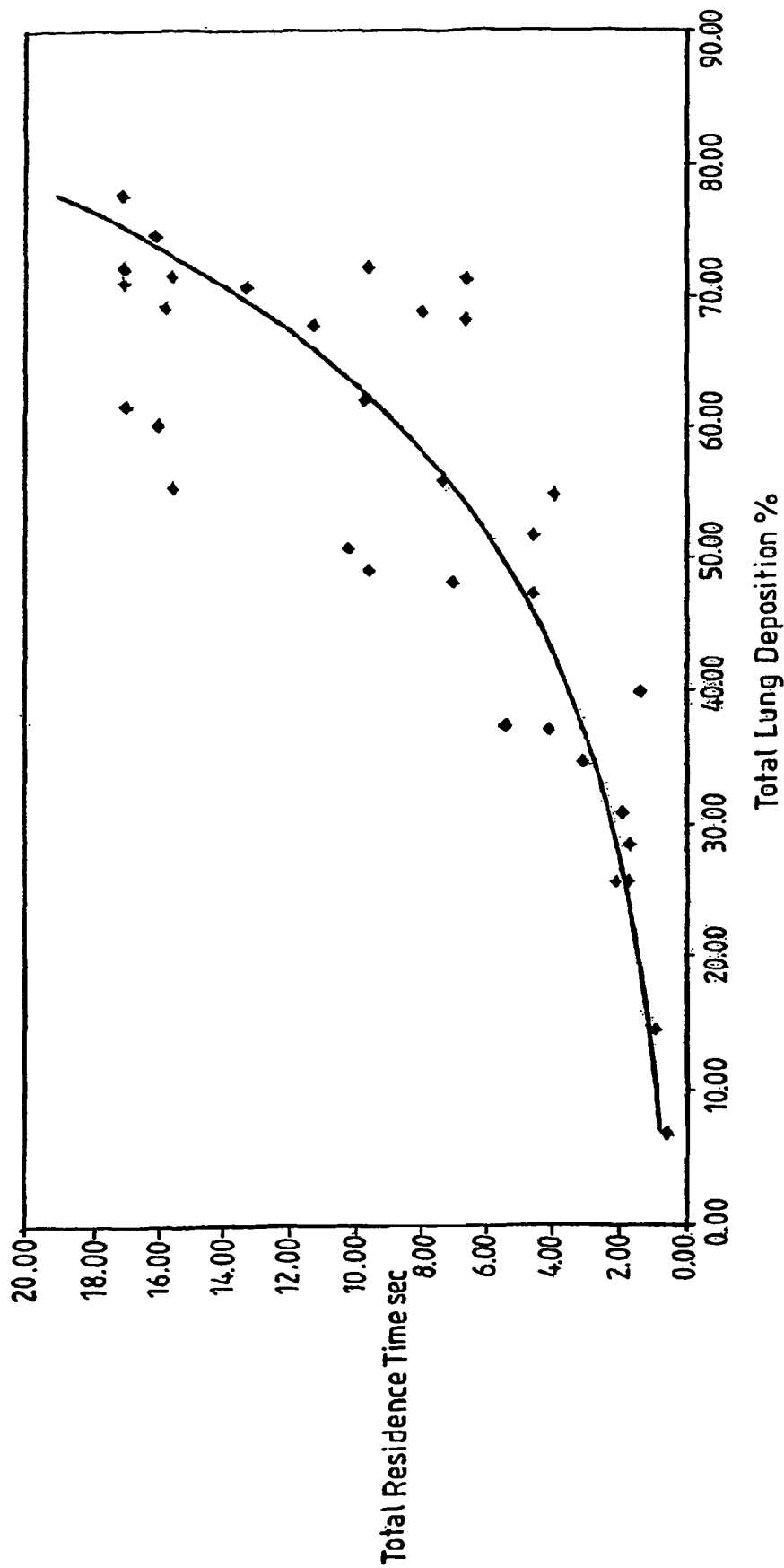

| | | |
|---|---|---|
| EP | 0 910 421 B1 | 3/2003 |
| GB | 2 320 900 A | 7/1998 |
| WO | WO 94/17370 | 8/1994 |
| WO | WO 98/52633 | 11/1998 |
| WO | WO 99/63946 | 12/1999 |
| WO | WO 00/24445 A1 | 5/2000 |
| WO | WO 00/38770 A3 | 7/2000 |
| WO | WO 00/50111 | 8/2000 |
| WO | WO 01/58514 A1 | 8/2001 |
| WO | WO 02/09574 A2 | 2/2002 |
| WO | WO 02/058771 A1 | 8/2002 |
| WO | WO 03/059423 A1 | 7/2003 |

* cited by examiner

Effect of "aerosol-hold" time on exhaled aerosol

FIG. 2.

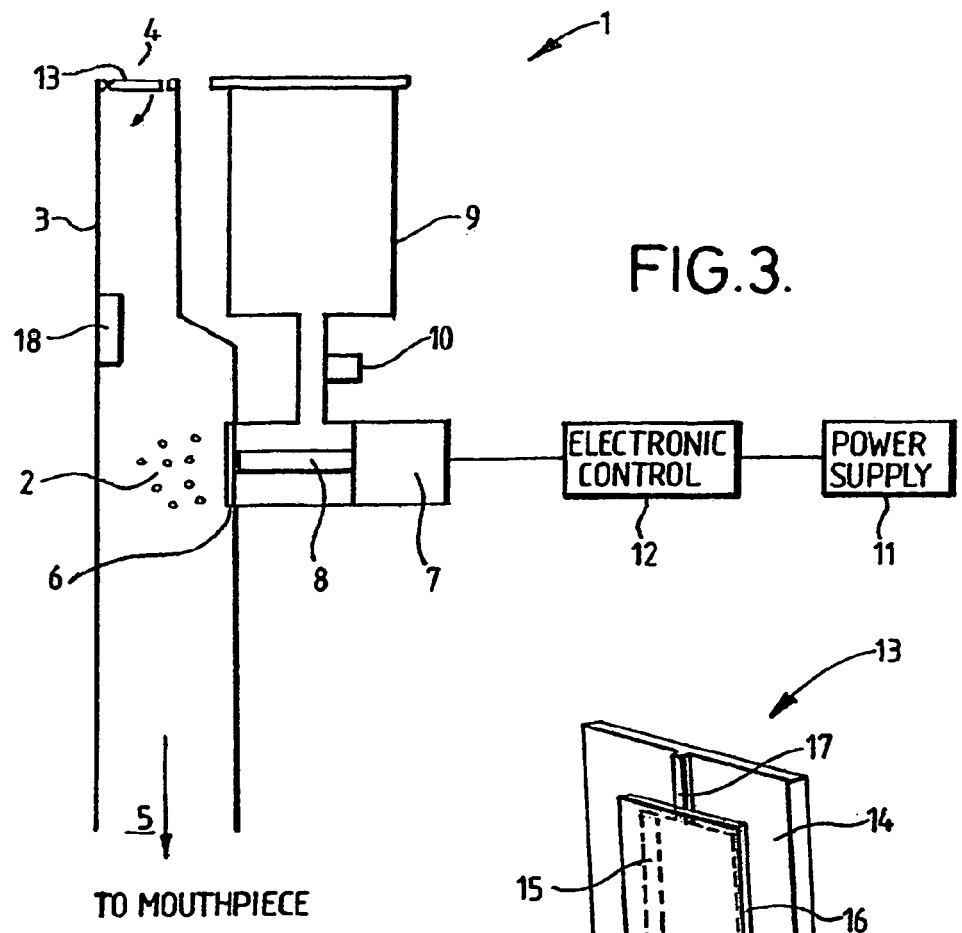
FIG.3.
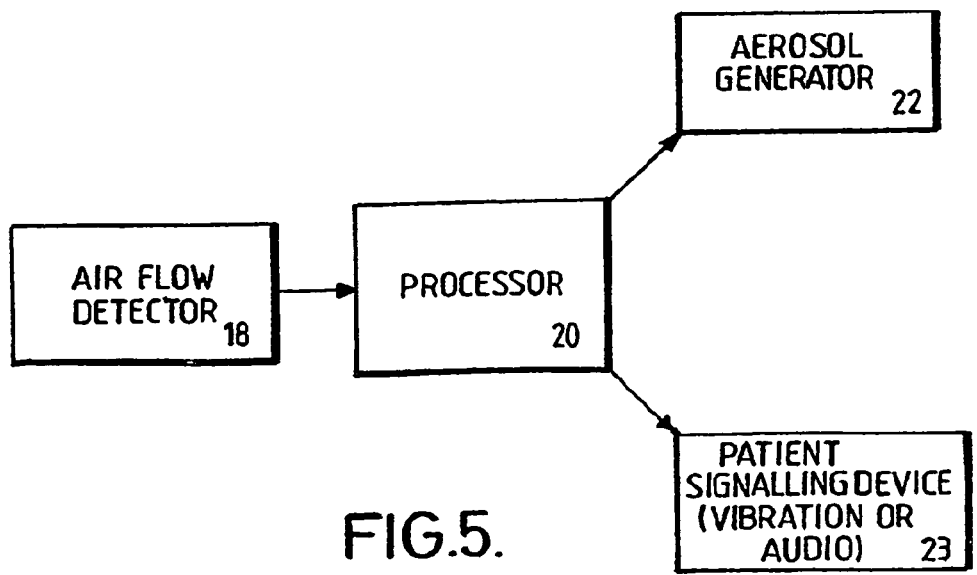
FIG.4.
FIG.5.

INHALATION METHOD AND APPARATUS

The present invention relates to a method of generating signals in a nebulizer, and to a drug delivery apparatus.

A number of devices are available for delivering a drug into the lungs of a patient. A pneumatic or jet type nebulizer is particularly effective in supplying an aerosolized drug for inhalation, but other types of nebulizer are also available, such as ultrasonic type nebulizers in which the drug to be atomized is forced through a mesh by vibration of a piezoelectric crystal, whereupon the droplets passing through the mesh are entrained in the air being inhaled by the patient. The gauge of the mesh determines the size of the droplets which enter the airstream. Electrohydrodynamic (EHD) nebulizers and capillary micro jet nebulizers are also known. Alternatively, a dosimetric spacer can be used. When using a spacer, the drug is introduced into a holding chamber of the spacer, either in areosolized form, or by loading the air within the holding chamber with the drug in powdered form. The patient breathes from the holding chamber thereby inhaling the drug laden air. Such spacers are particularly effective when treating children or elderly patients, and for use with certain drugs. The drug is normally delivered over a number of breaths.

An example of a mesh type nebulizer is shown in WO 99/63946, and examples of EHD and capillary micro jets nebulizers can be found in WO 00/38770 and U.S. Pat. No. 6,119,953 respectively, and we hereby import these disclosures in their entirety by this reference.

A pneumatic nebulizer is shown in EP 0627266 A2 in which air from a pressurized air source issues from an air outlet hole around which are disposed holes through which the liquid to be atomized is drawn out from a main reservoir. Each of these holes is within a groove forming a secondary reservoir around the air outlet hole. A deflector bar is located across and in the path of the air issuing from the air outlet so that as it issues from the air outlet, it is immediately deflected across the top of the liquid outlet holes thereby creating low pressure regions drawing the liquid up from the main reservoir beneath, and atomizing that liquid as it is drawn from the holes. The droplets generated in this way are carried to the patient for inhalation. Atomization can be switched on and off by switching on and off the pressurized air supply to the nebulizer.

European patent publication number 0910421 discloses a nebulizer, manufactured under the name Halolite, which delivers a drug during the first half of the patients inhalation in order to maximise lung deposition. The apparatus is interactive in that it measures the duration of a patient's inhalation and calculates a time period that is one half of an average of the patient's duration of inhalation. It is therefore able to match the delivery of the drug with the inhalation profile of the patient and takes account of changes in the patient's inhalation duration over time. It does not require the patient to perform a specific inhalation manoeuvre.

A drug delivery system described in WO98/52633, called the Akita system is known in which aerosolized drug is delivered to a patient in an airstream under a positive pressure delivered at 15 liters per minute up to a volume equivalent to 80% respiratory capacity. Respiratory capacity is defined as the inhalation volume measured from the end of a normal tidal exhalation to maximum lung capacity. The system includes controlled inhalation flow which prevents air from being delivered more quickly. This has the effect of lengthening the duration of inhalation. The system directs the patient when to breathe in, when to hold his breath, and when to exhale. Thus, it is arranged such that the patient, upon filling his lungs to capacity with air is instructed by the system to hold his breath for a period typically of the order of 5 to 9 seconds. The patient is then indicated to exhale. This breathing pattern is repeated until the drug has been completely delivered. Such a system is effective in delivering a high proportion of the drug to the lungs since the residence time of the drug in the lungs is relatively long, in this case at least 5 seconds, and for most of the drug rather longer than this. As a result, on exhalation, most of the drug has sedimented within the lungs such that it will not be exhausted from the lungs during exhalation.

However, the Akita system must first be set up with the patient in a clinic since the system must know the respiratory capacity of the patient in order to indicate the beginning of the breath hold step at the appropriate time. Different patients will have very different respiratory capacities depending on various factors including age, body size and the effect of any respiratory diseases. In addition, the duration of the breath hold must also be customised for particular patients to ensure that the patient will not suffer distress during the use of the system. If the breath hold is too long, then the patient will be unable to continue the treatment over a number breaths without suffering such distress. In addition, as the patient's symptoms change, then the system will need to be reconfigured to take account of this by another visit to a clinic.

According to a first aspect of the present invention, a method of generating signals in a nebulizer through which a person inhales to generate an inhaled airstream, comprises the steps of detecting the commencement of inhalation, signalling to the person to cease inhalation after a pre-set period of time has elapsed from the detection of the commencement of breathing; and adjusting the pre-set period of time for subsequent inhalations depending on the time the person takes to stop inhaling after being signalled.

In order to be responsive to the person using the nebulizer, the pre-set period of time may be increased if the time taken to stop inhaling exceeds a first threshold time, and may be decreased if the time taken to stop inhaling is less than a second threshold time. The first threshold time is normally greater than or equal to the second threshold time. The first threshold time is preferably about 0.5 seconds. The first threshold time may be in the range of 0.25 to 0.75 seconds, preferably in the range of 0.35 to 0.65 seconds, and most preferably in the range 0.45 to 0.55 seconds.

The second threshold time is preferably is about 0.3 seconds. It may be in the range of minus 0.2 to 0.5 seconds, preferably 0 to 0.4 seconds and most preferably 0.25 to 0.35 seconds.

The method preferably further comprises the steps of detecting the end of inhalation and calculating the period of inhalation and the period of exhalation. This then allows all of the calculations necessary to be made. The method may include the step of calculating the inhalation to exhalation (I:E) ratio, and if it is greater than a third threshold, increasing the preset period of time. In this case, the third threshold of time is preferably about 1. The method may also include the step of calculating the I:E ratio, and if it is less than a fourth threshold, the preset period of time can be disclosed. In this case, the fourth threshold of time is preferably about one third.

It will be appreciated that the nebulizer can be set up using the above mentioned method before it is used to deliver a drug. Alternatively, it can be done at the same time, and the nebulizer further comprises the step of delivering an aerosolized substance into at least a part of the inhaled air stream. Aerosol delivery is normally ceased before signalling to the person to cease inhalation. The aerosol delivery is ceased preferably at least one second before signalling to the person, and most preferably at least two seconds before signalling to the person.

The time taken for the person to stop inhaling in response to the signal has been found to be a good indication of whether or not the patient is experiencing distress, and so the pre-set period of time can be adjusted to accommodate the patient concerned and his particular requirements. This can be done without needing to visit a clinic. For example, if the person takes a relatively long time to stop inhaling, that is an indication that the pre-set period of time following the detection of the commencement or breathing can be lengthened. Conversely, if a person ceases to inhale very quickly after he is signalled to do so, or if he stops inhaling before signalled to stop, that will be an indication that the duration of the pre-set period of time is too long. The pre-set period can then be adjusted accordingly.

According to a second aspect of the invention, a drug delivery apparatus arranged to deliver aerosolized drug into an inhaled airstream of a person comprises, an airflow sensor for detecting the inhaled airstream, a signalling device arranged to give signals to the person, and a controller arranged to control the operation of the signalling device on the basis of the inhaled airstream detected by the flow sensor, whereby the controller causes the signalling device to signal to the person to cease inhalation after a pre-set period of time following the detection of inhalation; and adjusts the pre-set period of time for subsequent inhalations depending on the time the person takes to stop inhaling after being signalled.

The apparatus preferably includes an airflow regulator for restricting the speed of the inhaled airstream through the device.

The signalling device may be any one or more of an audio device, a visual device and a vibrator device. The audio device might emit a tone or a buzz, the visual device may include a screen, such as an LCD screen, or simple lights, possibly in the form of LED's. The vibrator device can signal to the person by causing the apparatus to vibrate thereby signalling to the person to stop inhaling.

In addition, the controller preferably includes a calculator arranged to calculate the pre-set period of time. The controller may be formed using a microprocessor.

The invention will now be described by way of example only with reference to the drawings in which:

FIG. 1 is a graph in which the total residence time of a drug within the lungs is plotted against the percentage of the drug which is deposited within the lungs;

Figure 2:
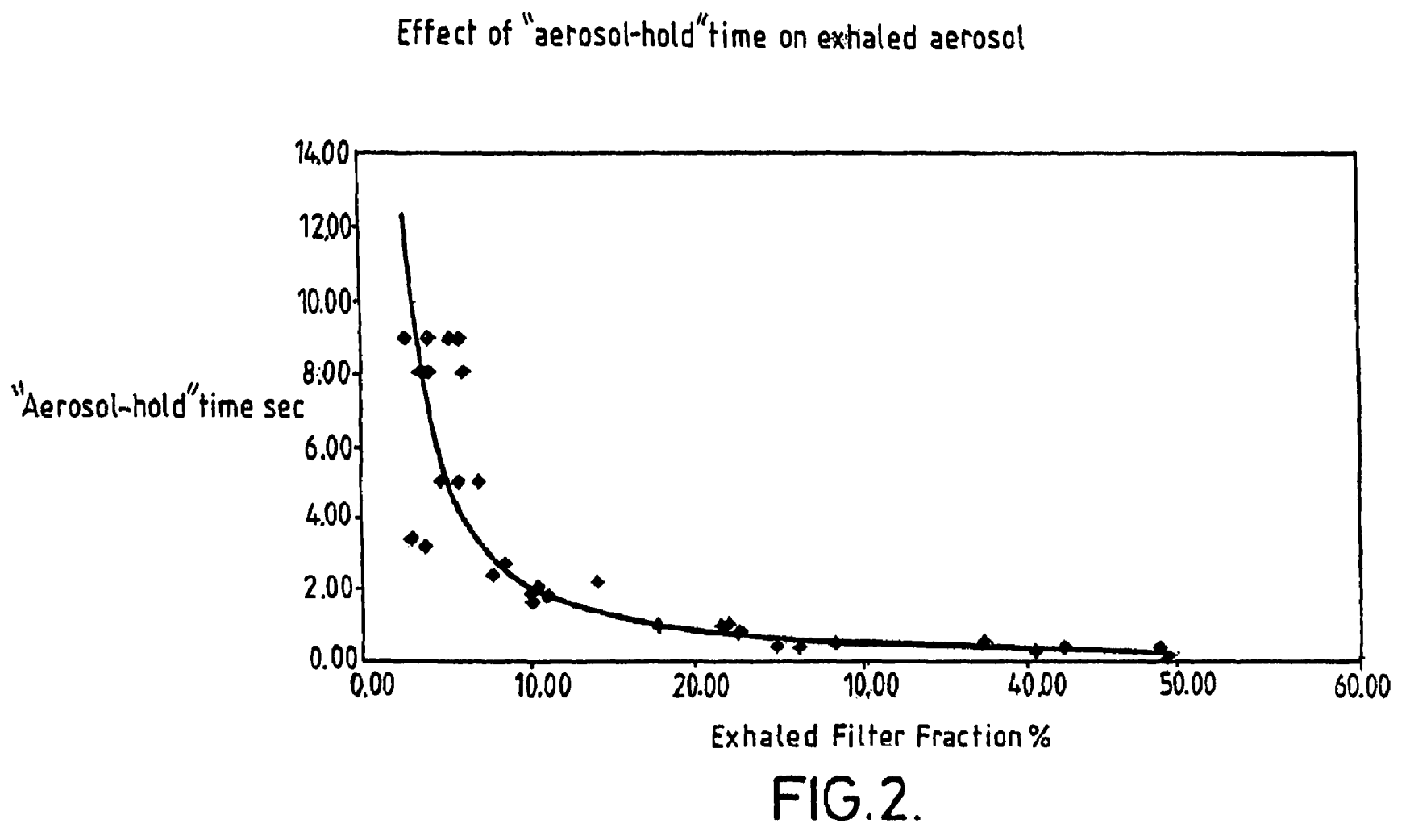

FIG. 2 is a graph plotting the aerosol hold/breath hold time against exhaled filter fraction;

FIG. 3 is a schematic drawing showing a nebulizer according to the present invention;

FIG. 4 is a perspective view of an airflow regulator of the nebulizer of FIG. 3;

FIG. 5 is a block diagram showing how the nebulizer is controlled, and how the patient is signalled in the nebulizer of FIG. 3;

FIG. 6 is flow diagram showing a method of operation of the nebulizer during which both drug delivery occurs and adjustment of the device to take account of the patient's breathing pattern occurs;

FIG. 7 is a graph showing the breathing pattern of a patient using the device of FIG. 3, with flow rate plotted against time;

FIG. 8 is a graph showing the target inhalation length plotted against the number of treatments carried out by three subjects;

FIG. 9 is a graph showing the treatment time plotted against the number of treatments for each of the three subjects;

FIG. 10 is a flow diagram showing a second method of operation of the device of FIG. 3 in which the operation of the device is optimised for a person prior to drug delivery.

EXPERIMENT

The Akita and Halolite system described in the introductory part of this application were used in an experiment in which a patient was supplied with a radio labelled aerosol. The aerosol was radio labelled to allow scintigraphic evaluation of the experiment. The systems were used in accordance with the manufacturers recommendations. A Sidestream nebulizer (Profile Respiratory Systems Ltd, Bognor Regis UK) and a nose clip were used. The Akita system provided a positive pressure stream of air for inhalation at 15 liters per minute up to a volume equivalent to 80% of respiratory capacity with a breath hold of between 5 and 9 seconds. A computer screen provided feedback to the patient as to the duration of inhalation and the breath holding pause required. In the case of the Akita System, on commencement of inhalation, the computer screen displays a numerical countdown of the period over which the patient should inhale. At the end of that period of time, the patient must hold his breath while the computer screen displays a further countdown of time until the patient is permitted to exhale. In the case of the Halolite System, the patient breathes in and out naturally without any feedback indicating to the person when to start inhaling, stop inhaling or carry out a breath hold. In fact, with the Halolite, since the person is intended to breathe in a slow relaxed manner, there will not be any breath hold period. However, since the atomisation stops before the end of the breath, there is a period of time during which the patient is still inhaling, but no aerosol is reaching the person's lungs. This period of time is referred to in this specification as the "aerosol hold time". This contrasts with the Akita System in which atomisation occurs during the entire inhalation phase, and only stops once the patient begins his breath hold. Therefore, the aerosol hold time and the breath hold time are rather different, but have the same effect of defining a minimum period during which the aerosol is resident within the lung. After the breath hold the subject exhales through a filter in order to trap any of the aerosol.

A treatment time of between 5 and 12 minutes was needed to deliver a set dose of 0.4 ml of Tc-DTPA from a 2.5 ml nebulizer fill.

A scintigraphic evaluation of the patients was carried out in order to identify how much of the radio labelled aerosol remained in the lungs of the patients. The results from both systems were analysed with respect to the patients breathing parameters. The results of the experiment are shown in FIGS. 1 and 2. In FIG. 1, the total residence time of the drug within the lungs is plotted against the total lung deposition as a percentage of the total aerosol delivered. It will be seen clearly that lung deposition increases with the total residence time. For example, a total residence time of 2 seconds is likely to result in less than 30% of the aerosol being deposited in the lungs, whereas doubling the residence time to 4 seconds will typically give a total lung deposition of more than 40%. By the time the total residence time reaches 12 seconds, the lung deposition reaches about two thirds of the aerosol delivered.

FIG. 2 is a graph in which the aerosol hold time (Halolite System) and breath hold time (Akita System) is plotted against the exhaled filter fraction. The exhaled fraction is reduced with increasing aerosol hold time. It indicated that for a aerosol hold time in the order of 1 second exhaled losses are in the region of 15-20% but if the aerosol hold time is increased to 2 seconds the losses are reduced to 10%. Increasing the aerosol hold time allows more time for the aerosol to deposit in the lung, as the principal method of deposition for particles of this size is sedimentation, which is time dependent.

The overall conclusion of this experiment is that the longer the aerosol is resident within the lungs, the higher the total lung deposition. This can be achieved both by the patient holding his breath following inhalation, and also by increasing the total inhalation time of the patient.

Description of Apparatus:

Referring now to FIG. 3, a drug delivery apparatus is shown which is a mesh type nebulizer 1 for generating an aerosol indicated generally at 2 in a passageway 3. The passageway 3 has an inlet 4 through which air enters it, and at its opposite end 5 the air passing through the passageway 3 is led to a mouthpiece or the like (not shown). During operation of the nebulizer 1, the aerosol 2 is entrained in the airflow leading to the mouthpiece. Nebulization takes place by a drug being forced through a mesh plate 6 by using an ultrasonic transducer 7 which drives a horn 8 to vibrate in the region of the mesh plate 6. The horn 8 is located close to the rear face of the mesh plate 6 and is caused to vibrate by the ultrasonic transducer 7, whereby the aerosol 2 is generated from the front face of the mesh plate 6. The substance to be atomised into an aerosol 2 is in fluid contact with the rear face of the mesh plate 6 and it is this that is driven through the holes of the mesh plate 6 by the vibrating horn 8.

During each treatment, a certain volume of the substance to be atomised is located in a reservoir 9 which is located above the mesh plate 6 in which to feed the substance to be atomised to its rear face. A fluid sensor 10 is located between the reservoir 9 and the mesh plate 6 such that once the substance to be atomised has substantially all been aerosolized, this is detected so that the ultrasonic transducer 7 may be switched off at the end of treatment.

A power supply 11 is used to power the atomiser since power is required to drive aerosolization. An electronic controller 12 controls the ultrasonic transducer 7 so that, for example, once the fluid sensor 10 senses that there is no liquid remaining to be atomised, the ultrasonic transducer 7 will be switched off. In addition, a more sophisticated control device can be used here such that the patient's breathing is measured, and atomisation only occurs during the inhalation part of a patient's breathing pattern.

An airflow regulator 13 is located in the passageway 3. This is shown in more detail in FIG. 4 from which it will be seen that the regulator 13 includes a frame 14 having an interior edge 15 (shown in dotted lines) which defines an aperture through which air must pass if it is to enter the passageway 3. A resilient flap 16 is located in front of the aperture located in the frame 14, and a rib 17 lying on the frame 14 acts as a spacer to prevent the flap 16 from completely closing the aperture. The flap 16 is typically made of a resilient silicone material. This means that any airflow through the regulator 13 which passes through the aperture and then against the flap 16 will cause the flap 16 to be deflected away from the frame 14 allowing the air to pass relatively freely. However, airflow passing the opposite way will cause the flap 16 to close, and the aperture will be severely restricted allowing a limited airflow to pass. The resilient nature of the flap will tend to offer more resistance to the airflow the greater the pressure difference on the opposite sides of the frame 14. This airflow regulator, therefore, limits the rate at which air passes through the passageway 3 towards the mouthpiece.

The nebulizer also includes an airflow detector 18 which is able to measure both the direction of airflow through the passageway 3 and the velocity of the airflow. In this embodiment, it is indicated to be located within the passageway 3, but could be located in various other positions, even in the mouthpiece. The detector 18 may be any one of a variety of different types of detector, such as a temperature sensor, a pressure sensor, a microphone type sensor or a mechanical sensor which is deflected by the airflow. The type of sensor used is not an important factor in this invention.

The basic operation of this nebulizer will now be described. Firstly, the patient will pour a certain volume of the substance to be atomised into the reservoir 9. The reservoir 9 may be sized such that it will exactly hold the appropriate volume of the substance that is required. The patient can then begin to breathe in and out through the mouthpiece. Upon commencement of inhalation, the airflow detector 18 will detect the commencement of inhalation, and the electronic control 12 will cause the ultrasonic transducer 7 to vibrate, thereby driving the horn 8 to cause aerosolization of the substance to be atomised. As the substance is aerosolized, the reservoir 9 empties, and once the level of the substance drops below the fluid sensor 10, the electronic control 12 switches off the ultrasonic transducer.

During inhalation, the airflow regulator 13 operates to regulate the speed of air passing through the passageway 3 and to the patient, thereby lengthening the patient's inhalation phase. Once the patient stops inhaling, the airflow detector 18 will detect this, and will cause the electronic control 12 to stop the ultrasonic transducer 7 driving the horn 8 until the next inhalation phase is detected. Alternatively, the electronic control 12 might be arranged only to drive the ultrasonic transducer during, say, the first 50% of the inhalation phase of the patient. To achieve this, the duration of inhalation of the previous few inhalations as measured by the airflow detector 18 will need to be averaged, and half of this averaged duration will be the period for which the electronic control 12 causes the ultrasonic transducer 7 to drive the horn 8 to atomise the substance. Of course, it will be appreciated that atomisation might occur during 60%, 70%, 80% or any other suitable proportion of the inhalation phase.

During exhalation, the exhaled air might be exhausted from an outlet in the mouthpiece, or alternatively might flow back up the passageway 3 towards the airflow regulator 13 which will open to allow the air to be exhausted freely. It is preferable to locate the airflow detector 18 as close to the mouthpiece as possible, and where the exhaled air is exhausted from an outlet in the mouthpiece, it will normally be appropriate to locate the airflow detector 18 within the mouthpiece.

Also, the airflow regulator 13 may be located anywhere in the device where it will restrict the airflow leading to the patient. However, it is preferred that it is located upstream of the point at which the aerosol is generated during inhalation. That way, the aerosol will not be removed from the airstream by the constriction caused by the airflow regulator 13.

FIG. 5 shows the arrangement of the nebulizer in block diagram form. From it, one block refers to the airflow detector 18 shown in FIG. 3. The output from the detector 18 is passed to a processor 20 which controls the aerosol generator 22 and a patient signalling device 23. The processor 20 will include the electronic control 12 shown in FIG. 3, as well as other elements. The aerosol generator 22 refers to a combination of the mesh plate 6, the ultrasonic transducer 7, the horn 8 and the reservoir 9 in the nebulizer 1 shown in FIG. 3. The patient signalling device 23 is not shown in FIG. 3, but is some form of device which generates signals for the patient when to carry out certain breathing manoeuvres. According to one arrangement, this could be a vibrator device which causes the nebulizer 1 to gently vibrate to signal when to carry out particular manoeuvres. Alternatively, it can be an audio device which uses sounds to signal to the patient when to carry out the manoeuvres. It could even be a visual device where the patient is signalled to carry out particular manoeuvres on the basis of visual signals which may be lights or an LCD screen. The signalling device 23 could be a combination of these systems. The operation of the blocks shown in FIG. 5 will become clearer when the overall operation of the device is described with reference to FIG. 6.

Example 1

Figure 6:
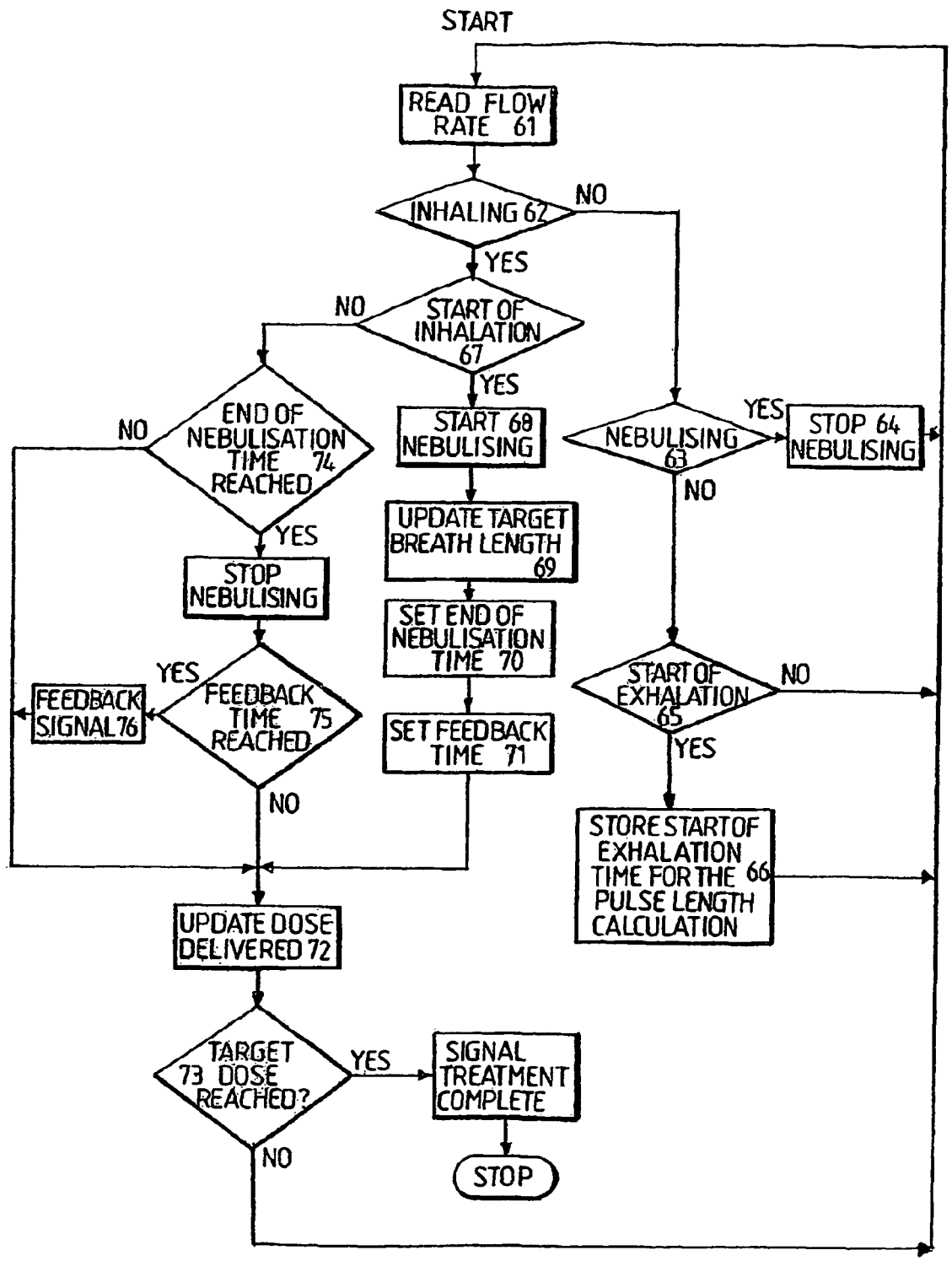

FIG. 6 is a flow diagram showing one method of operation of the drug delivery apparatus shown in FIG. 3. It should be appreciated that this method can be applied to other types of nebulizer, and is not limited to operating in connection with an ultrasonic mesh type nebulizer.

The first step is for the processor 20 to read the flow rate from the airflow detector 18. If the person has not yet started to inhale, box 62 will return a "NO" and the processor 20 will ask whether or not the aerosol generator 22 is nebulizing. If it is, then the processor 20 will stop the aerosol generator 22 from operating and return to the "START" if it is not nebulizing, then the processor 20 will read the airflow detector 18 to see whether or not the person has started to exhale. If not, it will again return to the "START". If the person has started to exhale, then the processor 20 will store the start of exhalation time for a later pulse length calculation. The details of this calculation will be explained later in the specification. Once this has occurred, the processor 20 will return to the "START".

Once the person starts inhaling, when the processor 20 reads the flow rate 61 from the airflow detector 18, he will found to be inhaling 62, and so the processor will then ask whether or not it is the start of inhalation 67. Since it is the start of inhalation, the processor 20 will then cause the aerosol generator 22 to begin nebulizing 68. It will then update the target breath length 69 based on the previous inhalation data and time between inhalations. This will be explained further later in the specification, but the target breath length is the period of time from commencement of inhalation to the moment the person is signalled to stop inhaling. Once the target breath length has been updated, the nebulization time is set to end, normally sometime before the end of target breath length so that the last part of the air inhaled by the person, and which stays in the upper airways, is not laden with the aerosol which would be wasted. This provides an appropriate aerosol hold time in the region of 1 to 2 seconds without the person needing to hold his or her breath. Calculation of the nebulization time will be described later in this specification. Once it has been done, a running calculation is made of the dose that has been delivered up to that point, which is updated. On the assumption that the target dose has not yet been reached, the processor returns to the "START". Since the patient has only just began to inhale, the flow rate supplied by the airflow detector 18 will indicate that the person is still inhaling, and since the last loop through the flow chart indicated that it was the start of inhalation, this time it is not the start of inhalation, and so the processor 20 will then calculate whether or not the end of the nebulization time has been reached. On the assumption that it has not been reached, the running total of the dose delivered is updated, and assuming that the target dose has not yet been reached, the processor 20 returns to the "START". Once the end of the nebulization time has been reached, nebulization will stop, and the processor will then ask whether the feedback time has been reached 75. Since nebulization is intended to stop before the patient finishes inhaling, typically between 1 and 2 seconds before hand, initially, the feedback time reached box is likely to return a NO. The dose is updated in box 72, and the process returns to the START. Once the feedback time has been reached, then the person is signalled with a feedback signal, and the processor returns to the START. The feedback signal to the person is an indication to him to stop inhaling. This signal may be by vibration, audio or visual. In the unlikely event the patient exhaled before the end of nebulization time is reached, nebulization will stop (box 63/64). The patient will now continue to inhale until the feedback time is reached (box 75).

Once the feedback signal is produced by the signalling device 23, the person should quickly stop inhaling, but is likely to continue to do so for the short period of time it takes him to react. Therefore, the next few circuits through the flow chart by the processor 20 will find that the patient is still inhaling. Once the person does actually stop inhaling, the time taken by the person to stop inhaling from the characterised signal is measured. In addition, the time between inhalations is also measured.

This process will be repeated for each breath until the target dose is reached when the nebulizer is switched off and the patient is indicated to stop. The nebulizer might also switch itself off. However, the information concerning the target breath length is retained for future operations.

Figure 7:
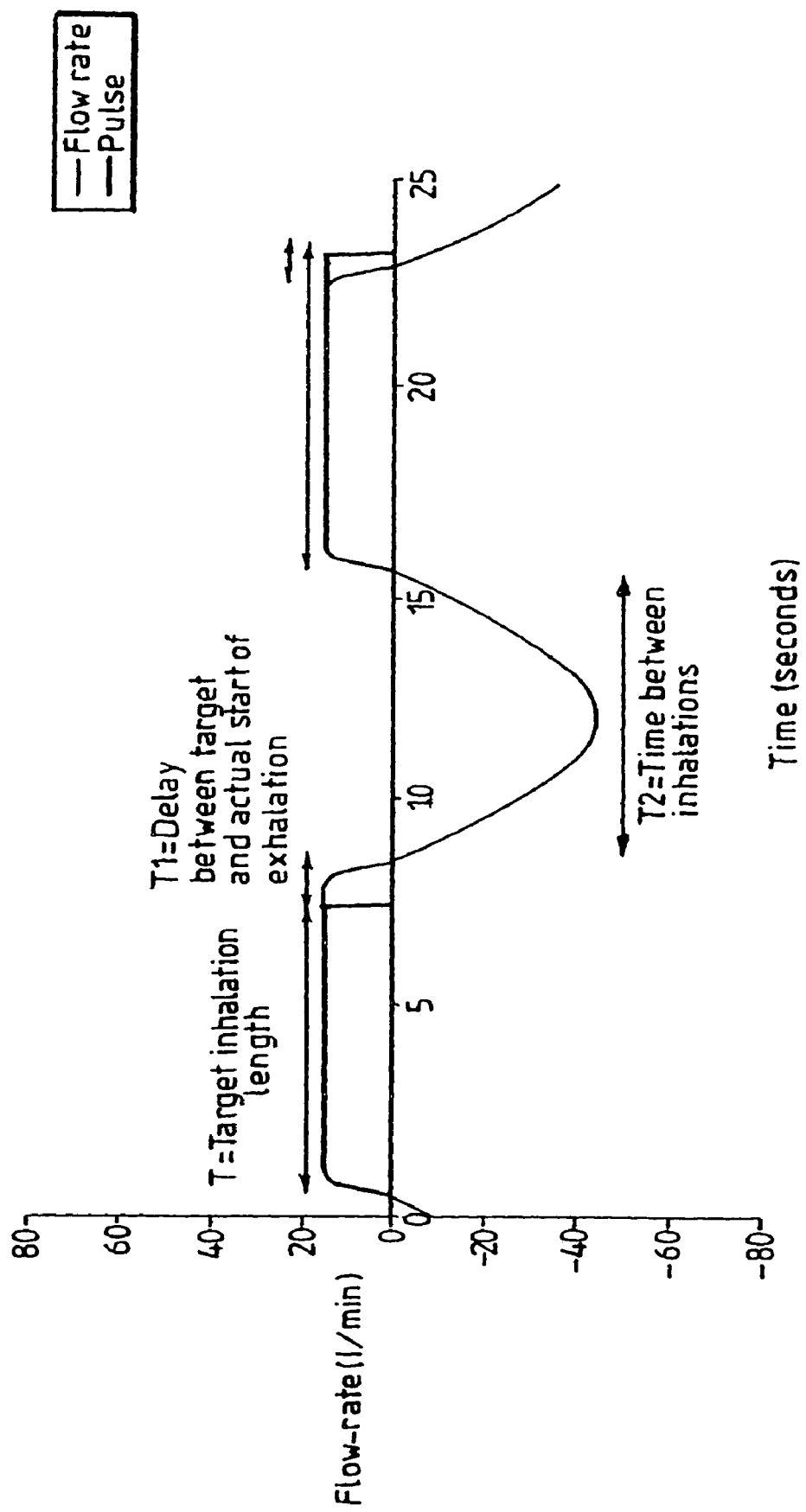

FIG. 7 is graph showing the breathing pattern of a person during two inhalations using this apparatus. During inhalation, because of the airflow regulator 13, the inhalation flow is limited and therefore the graph shows a flat top to the inhalation phase. The calculated target inhalation length is indicated (T), at the end of which the patient is signalled to exhale. The period of time labelled T1 on the graph in FIG. 7 is the time it takes for the person to actually start exhaling. It will be seen from the graph that exhalation is not restricted in the same way as the inhalation phase, and so the flow rate is quite a deep trough. The period over which the flow rate is negative, where exhalation is taking place, is indicated as T2. Both of these time periods are measured during the method that was described with reference to FIG. 6.

Some testing of the invention has taken place to establish how long T1 and T2 should normally be, and when the target inhalation length should be changed, and by how much.

Example 2

In this example, the device as described in FIGS. 3 to 5 is used to control the duration of a person's inhalation. The duration of inhalation to maximise the aerosol delivery in each inhalation. In practice, the maximum acceptable inhalation time is about 9 seconds, or 70-80% of respiratory capacity. Instead of a breath hold period of two seconds, this part of the breathing manoeuvre is incorporated into the inhalation phase as a period of non-atomisation at the end of the inhalation phase. The inhalation flow rate is limited by the airflow regulator 13 to give a maximum inhalation flow of 250 ml per second.

Although it is possible to measure the respiratory capacity of the person, it is preferred just to start at a low inhalation length, adjusting subsequent breath lengths according to how the patient copes with the previous breath. Measuring the inhalation capacity of a person adds complication both in terms of the apparatus and in terms of what the person must do during set-up. The target inhalation length can then be carried over to the next treatment. Thus, after the first few treatments, the target inhalation duration would be expected to increase to a level appropriate to that person. The adaptive nature of this device allows an automatic increase or reduction in the target inhalation length if the patient begins to struggle as a result of exacerbation. The person may be able to reduce the overall treatment time as he or she learns how to maximise the inhalation time.

In this example, the initial target inhalation length is set to the minimum value of 3 seconds, which includes the two second aerosol hold period. This means that the aerosol is delivered during the first second of inhalation, and no aerosol is delivered during the second or third second. At the end of the three second period, the signalling device 23 signals to the patient to exhale, and the time delay between the end of the target inhalation length and the actual start of exhalation is measured. If the delay between the target inhalation length and the actual start of exhalation is greater than a first preset threshold, then the patient may be finding the target inhalation volume too small, and could be expected to cope with an increased inhalation time. If it is less than a second pre-set threshold which may be different to the first threshold, then the patient may be finding the target inhalation volume too large, and this could be reduced.

In addition, if the time between inhalations is shorter than the last inhalation time (for example if I:E is more than one) then the patient may be desperate to reach the next inhalation, suggesting the target inhalation length is not long enough. If the time between inhalations exceeds 3 times the inhalation time then it is assumed that the patient needs to take a rest between inhalations and the target inhalation length is too long. The target inhalation length can be adjusted accordingly.

During experiments, it has been found that the first threshold period beyond which the delay between the end of the target inhalation length and the start of exhalation above which the target inhalation length should be increased is about 0.5 seconds. The second threshold beneath which the target inhalation length should be shortened has been found to be about 0.3 seconds. The first threshold may be anywhere in the range of 0.25 to 0.75 seconds, preferably in the range 0.35 to 0.65 seconds and most preferably in the range between 0.45 and 0.55 seconds. The second threshold may be in the range of −0.2 seconds to 0.5 seconds, preferably between 0 to 0.4 seconds and most preferably between 0.25 and 0.35 seconds.

Where the delay between the target inhalation length and the start of exhalation falls outside of the thresholds, the target inhalation length of the following breath will be increased or decreased as appropriate, typically by not more than 10%, preferably by not more than 5%, most preferably by not more than 2%, but with the optimum change by between 1% and 2%.

Where the I:E is calculated to be outside of the normal range, for example if it is more than one or less than one third, the target inhalation length can be increased or decreased as appropriate, typically by not more than 10%, preferably by not more than 5%, most preferably by not more than 2%, but with the optimum change being between 1% and 2%. Of course, although in this example, the target inhalation length is adjusted when the I:E ratio is more than 1, or less than one third, these are only examples of values which have been found appropriate, and this specification is not limited to those values.

Reference is made above to the setting of the nebulization time which is set during the method described with reference to FIG. 6. To expand this further, it should be understood that nebulization occurs in the form a pulse which, in this case, commences with the detection of the commencement of inhalation and stops before the end of the target inhalation length. Because, in this example, the aerosol hold period has been set to 2 seconds, this means that the nebulization pulse length will be 1 second. However, assuming that the person finds the target inhalation period of 3 seconds to be too short, this will be extended over the period of a number of breaths, and all of that increase will translate into an increase in the length of the nebulization pulse. The longer the nebulization pulse, the more drugs can be delivered per breath, and the quicker the treatment is completed.

Example 3

In an experiment, three people were subjected to a regimen where the various thresholds described above were different. Three subjects were given ten consecutive treatments using the device. For each of them, the target inhalation length was initially set to the minimum value of three seconds, including the two second aerosol hold period (the last two seconds of the inhalation phase). For the first subject, the first threshold was set at 0.25 seconds and the second threshold was set at −0.05 seconds (i.e. 0.05 seconds before the patient is signalled). The second subject had a device set with the first threshold at 0.60 seconds and the second threshold set to be 0.3 seconds. The third subject had a device set with the first threshold of 0.50 seconds, and the second threshold of 0.20 seconds.

Figure 8:
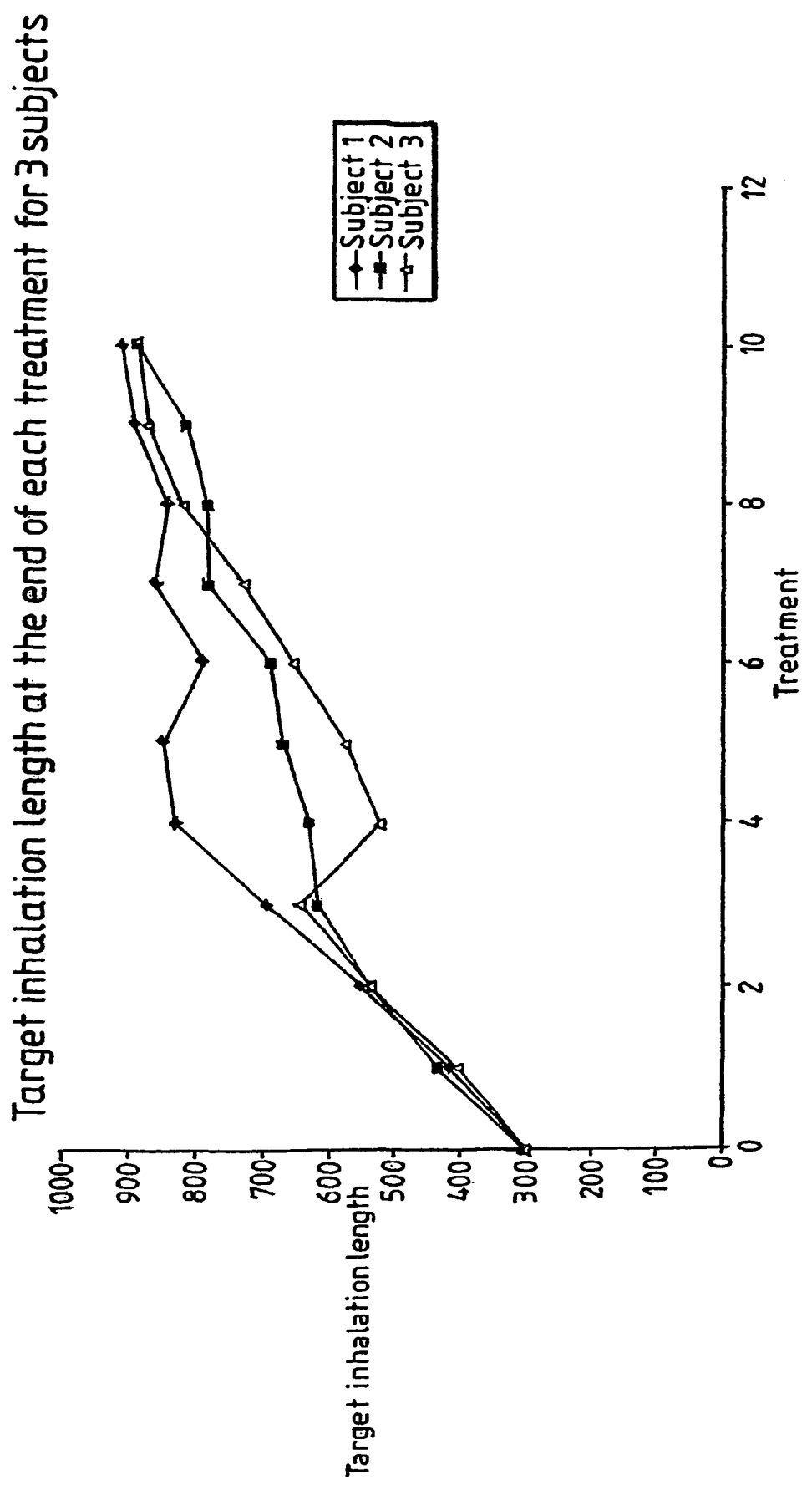
Figure 9:
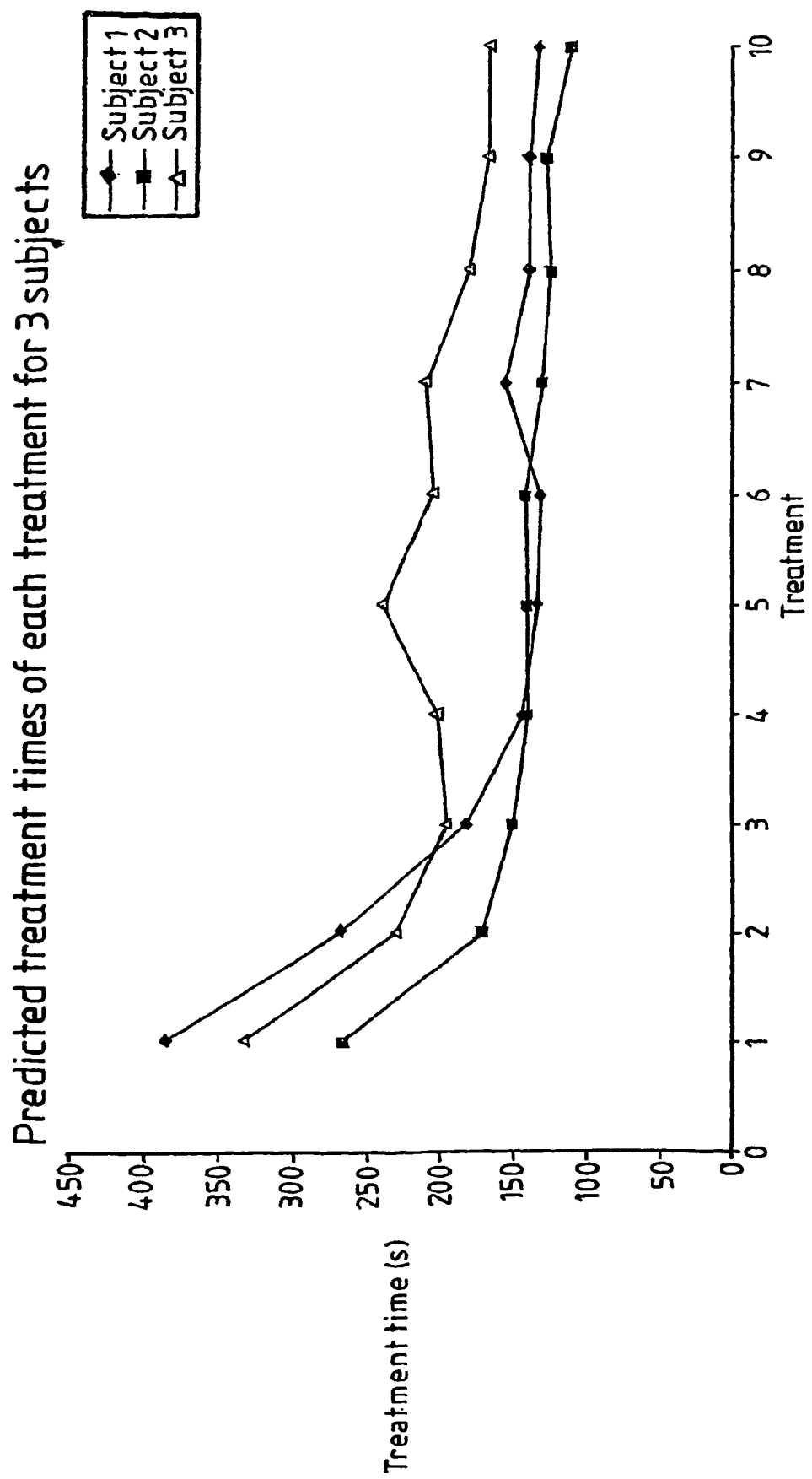

The results are plotted in FIGS. 8 and 9. It will be seen from FIG. 8 that subject 1 reached the maximum target inhalation length of 9 seconds within 5 treatments. All three subjects reached the target inhalation length within 10 treatments, and it will be seen that the target inhalation length adapts from treatment to treatment to take account of the symptoms of a patient. It will also be seen from FIG. 9 that the duration of each treatment drops significantly as the target inhalation lengths increase. Patients tend to comply with treatments much better when the treatment times are short. These three patients reached 70, 76, 112% of their respiratory capacity, indication that the system is very effective at maximising aerosol delivery without having to make separate measurements of respiratory capacity and programming these into the device.

In these examples of the use of the apparatus shown in FIGS. 3 and 4, the apparatus adapts to the person's breathing pattern during treatments. This means that the person does not need to attend a clinic to have the treatment regime programmed into the apparatus since the apparatus will make the appropriate adjustments. This is shown in the reduction in treatment times over the first few treatments. This has the benefit of making a significant reduction in the resources required by hospitals and clinics.

Example 4

Figure 10:
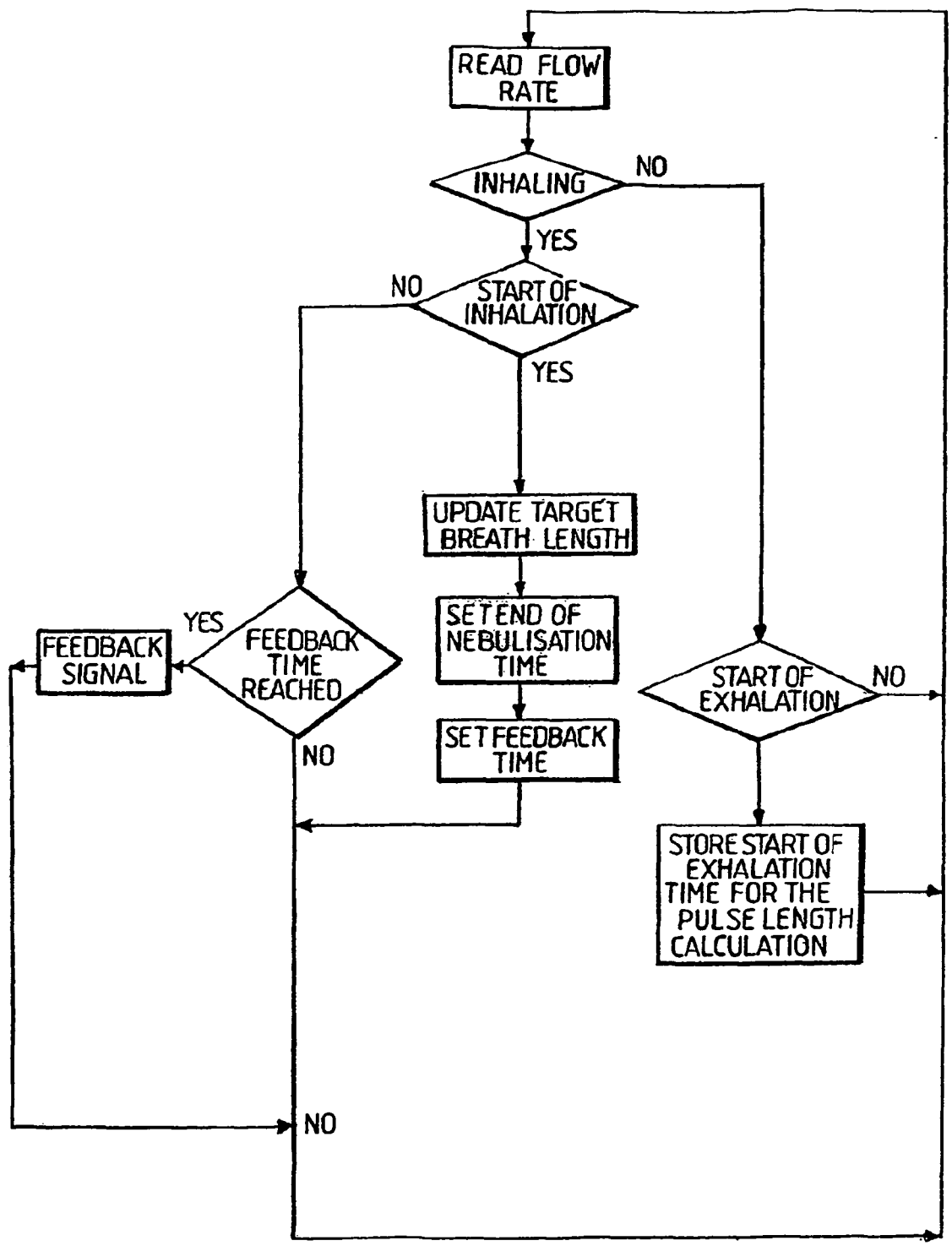

The apparatus can be used to adapt to a person without delivering any drug during a set up period. This means that before using the device for the delivery of a drug, the person can spend a small number of set up periods familiarising himself with the device and bringing it into a condition where the treatment time will be minimised at the first treatment. FIG. 10 is a flow chart showing how the apparatus is set up, similar to that shown in FIG. 6, but without the delivery of any of the substance to be atomised. The feedback signals are still given at the end of each target inhalation and the target breath length is updated after each breath to take account the time it takes for the patient to stop inhaling.

Firstly, the person setting up the device will switch the nebulizer on, but will not fill up the reservoir since he is setting up the device rather than receiving a treatment. It may be necessary to switch it to a set-up mode where the empty reservoir does not prevent the set-up process. Upon commencement of inhalation, the airflow detector 18 will detect the commencement of inhalation, but the electronic control will not allow the ultrasonic transducer 7 to vibrate since the device is being set up and is not delivering a drug to the person. During inhalation, the airflow regulator 13 operates to regulate the speed of air passing through the passageway 3, thereby lengthening the person's inhalation phase. Once inhalation stops, the airflow detector 18 will detect this.

From the flow chart of FIG. 10, the first step is for the processor to read the flow rate from the airflow detector 18. If the person has not yet started to inhale, the step indicated by the box labelled "inhaling" will return a "NO" and the processor will then ask whether or not the person has started to exhale. If not, the processor will return to the "START". If the person has started to exhale, then the processor 20 will store the start of exhalation time for a later pulse length calculation.

Once the person starts inhaling, when the processor 20 reads the flow rate from the airflow detector 18, he will be found to be inhaling and so the processor will then ask whether or not it is the start of inhalation. Where it is the start of inhalation, the target breath length will be updated and the feedback time set. The processor then returns to the "START". Since the person has only just begun to inhale, the flow rate supplied by the airflow detector 18 will indicate that the person is still inhaling since the last loop through the flow chart indicated that it was the start inhalation. The processor 20 will then calculate whether or not the target breath length has been reached. Again, assuming that the target breath length has not been reached, the processor 20 returns to the "START". If, however, the end of the target breath length has been reached, the patient is signalled with a feedback signal and the processor returns to the "START". The feedback signal to the person is an indication to him to stop inhaling.

Once the feedback signal is produced by the signalling device 23, the person should quickly stop inhaling, but is likely to continue to do so for the short period of time it takes him to react. Therefore, the next few circuits through the flow chart by the processor 20 will find that the patient is still inhaling. Once the person does actually stop inhaling, the time taken by the person to stop following the feedback signal is measured. In addition, the time between inhalations is also measured.

The calculations described above are carried out to see whether or not the target breath length needs to be changed, and this is updated accordingly when the person starts to inhale on the next breath. After a number of set up operations, the nebulizer can be used for treatment, with the target breath length much closer to the optimum breath length. Thus, from the very first delivery of a drug, the person is benefiting from the set up period in shorter treatment times.

It will be appreciated that, although a mesh type nebulizer is used in the device shown in FIGS. 3 to 5, other types of nebulizer may be equally appropriate. What is important is the adaptation of the target inhalation length to the patient's actual breathing pattern.

The invention claimed is:

1. A method of generating signals in a drug delivering apparatus through which a person inhales to generate an inhaled airstream, comprising the steps of:
   detecting the commencement of inhalation via a sensor;
   signalling to the person to cease inhalation after a pre-set period of time has elapsed from the detection of the commencement of breathing;
   detecting, via the sensor, a time the person takes to stop inhaling after being signalled; and
   adjusting the pre-set period of time for subsequent inhalations depending on the time the person takes to stop inhaling after being signalled.

2. A method according to claim 1, wherein the pre-set period of time is increased if the time taken to stop inhaling exceeds a first threshold time.

3. A method according to claim 1, wherein the pre-set period of time is decreased if the time taken to stop inhaling is less than a threshold time.

4. A method according to claim 2, wherein the pre-set period of time is decreased if the time taken to stop inhaling is less than a second threshold time and wherein the first threshold time is greater than or equal to the second threshold time.

5. A method according to claim 2, wherein the first threshold time is about 0.5 seconds.

6. A method according to claim 5, wherein the first threshold time is in the range of 0.25 to 0.75 seconds.

7. A method according to claim 5, wherein the first threshold time is in the range of 0.35 to 0.65 seconds.

8. A method according to claim 5, wherein the first threshold time is in the range of 0.45 to 0.55 seconds.

9. A method according to claim 3, wherein the second threshold time is about 0.3 seconds.

10. A method according to claim 9, wherein the second threshold time is in the range of −0.2 to 0.5 seconds.

11. A method according to claim 9, wherein the second threshold time is in the range of 0 to 0.4 seconds.

12. A method according to claim 9, wherein the second threshold time is in the range of 0.25 to 0.35 seconds.

13. A method according to claim 1, wherein the method further comprises calculating the period of inhalation and the period between inhalations.

14. A method according to claim 13, wherein the method further comprises the step of calculating an I:E ratio, and if it is greater than a third threshold, increasing the pre-set period of time.

15. A method according to claim 14, wherein the third threshold is about one.

16. A method according to claim 13, further comprising the step of calculating the I:E ratio, and if it is less than a fourth threshold, decreasing the pre-set period of time.

17. A method according to claim 16, wherein the fourth threshold is about one third.

18. A method according to claim 1, wherein the method further comprises the step of delivering an aerosolized substance into at least a part of the inhaled airstream.

19. A method according to claim 18, further comprising the step of ceasing aerosol delivery before signaling to the person to cease inhalation.

20. A method according to claim 19, wherein aerosol delivery is ceased at least two seconds before signalling to the person.

21. A drug delivery apparatus arranged to deliver aerosolized drug into an inhaled airstream of a person comprising:
   an airflow sensor for detecting the inhaled airstream;
   a signalling device arranged to give signals to the person; and
   a controller arranged to control the operation of the signalling device on the basis of the inhaled airstream detected by the flow sensor, wherein the controller is configured to:
      cause the signalling device to signal to the person to cease inhalation after a pre-set period of time following the detection of inhalation;
      detect, via the airflow sensor, a time the person takes to stop inhaling after being signaled; and adjust the pre-set period of time for subsequent inhalations depending on the detected time the person takes to stop inhaling after being signalled.

22. An apparatus according to claim 21, further comprising an airflow regulator for restricting the speed of the inhaled airstream through the apparatus.

23. An apparatus according to claim 21, further comprising an aerosol generator for aerosolizing the drug into the inhaled airstream.

24. An apparatus according to claim 21, wherein the signalling device is any one or more of: an audio device, a visual device and a vibrator device.

25. An apparatus according to claim 21, wherein the controller includes a calculator arranged to calculate the pre-set period of time.

26. An apparatus according to claim 21, wherein the controller is formed by a microprocessor.

27. A method according to claim 19, wherein aerosol delivery is ceased at least one second before signalling to the person.

\* \* \* \* \*